United States Patent [19]

Grey et al.

[11] 4,232,170

[45] Nov. 4, 1980

[54] PROCESS FOR HOMOGENEOUS HYDROGENATION OF ESTERS

[75] Inventors: Roger A. Grey, Denville; Guido P. Pez, Boonton, both of N.J.

[73] Assignee: Allied Chemical Corporation, Morris Township, Morris County, N.J.

[21] Appl. No.: 7,876

[22] Filed: Jan. 31, 1979

[51] Int. Cl.³ ............... C07C 69/675; C07C 31/38; C07C 27/04
[52] U.S. Cl. ................... 560/179; 568/842; 568/885; 423/415 A
[58] Field of Search ............... 568/885, 842; 560/179

[56] References Cited

U.S. PATENT DOCUMENTS

| | | | |
|---|---|---|---|
| 3,110,747 | 11/1963 | Mullineaux | 568/885 |
| 3,957,827 | 5/1976 | Lyons | 252/431 N |

FOREIGN PATENT DOCUMENTS 1246123 9/1971 United Kingdom ............... 260/429 R

OTHER PUBLICATIONS

Lyons, "J.C.S. Chem. Comm.," 1975, pp. 412–413.

Primary Examiner—Joseph E. Evans
Attorney, Agent, or Firm—Robert A. Harman

[57] ABSTRACT

A novel process is described for the homogeneous hydrogenation of carboxylic acid esters to primary alcohols utilizing anionic Group VIII metal hydride compositions as catalysts which contain phosphorus, arsenic or antimony organoligands. Use of these anionic catalysts allows the process to be conducted in solution under mild conditions of temperature and pressure with high selectivity and eliminates the disadvantages of utilizing heterogeneous catalysts. A process is also described for decarbonylating formate esters utilizing said compositions as catalysts.

8 Claims, No Drawings

PROCESS FOR HOMOGENEOUS HYDROGENATION OF ESTERS

BACKGROUND OF THE INVENTION

1. Field of the Invention

This invention relates to a process for homogeneously hydrogenating carboxylic acid esters to primary alcohols in solution under mild conditions utilizing anionic Group VIII metal hydride compositions as catalysts.

2. Brief Description of the Background of the Invention Including Prior Art

Carboxylic acid esters, as a class, are not readily susceptible to hydrogenation to produce primary alcohols under mild conditions. Generally, very forcing conditions are required, such as temperatures well above 150° C. together with reaction pressures in the order of 2000–3000 psig. In addition, the hydrogenation process generally requires a heterogeneous catalyst, which are frequently not selective such as Raney nickel, copper-chromite, or zinc-chromium oxide. See *Organic Reactions*, Vol. 8, pages 1–27 (John Wiley, 1954).

Catalytic hydrogenation of carboxylic acid esters represents an important industrial source of primary alcohols, which are useful in a wide variety of known applications such as in producing gums, resins, perfumes, wetting agents and the like. For example, 1-decanol is commercially produced by catalytic hydrogenation of coconut oil fatty acids and their esters under high pressure. Sulfonated derivatives of 1-decanol are useful as surface-active agents. Also, trifluoroethanol, $CF_3CH_2OH$, useful as an intermediate in producing the anesthetic, $CF_3CHClOCHF_2$, is produced by the heterogeneous catalytic hydrogenation of trifluoroethyltrifluoroacetate, $CF_3COOCH_2CF_3$, as described in U.S. Pat. No. 4,072,726 (Nychka et al. to Allied Chemical Corporation 1978).

Homogeneous catalytic hydrogenation of acyclic and cyclic carboxylic acid anhydrides to the corresponding esters and lactones by the use of soluble ruthenium catalysts is described in U.S. Pat. No. 3,957,827 (1976) and J.C.S. Chem. Comm. p. 412–413 (1975). However, no specific mention is made of the reduction of esters to the corresponding primary alcohols.

New and improved catalysts for catalytic hydrogenation of carboxylic esters to primary alcohols are constantly being searched for and especially for homogeneous catalysts that can overcome the known attendant disadvantages of the use of heterogeneous catalysts.

SUMMARY OF THE INVENTION

We have unexpectedly found that the anionic Group VIII metal hydride compositions, described by Guido Pez and Roger Grey in U.S. Application, Ser. No. 972,147 now abandoned are very effective catalysts in the hydrogenation of carboxylic acid esters to primary alcohols.

The invention process generally involves subjecting a solution of a carboxylic acid ester and catalyst composition, neat or in a suitable inert solvent, to an atmosphere containing hydrogen gas under mild conditions, preferably at temperatures below 150° C. and pressures below 150 psig, whereby high yields and high selectivities of the resulting primary alcohol are obtained.

In accordance with this invention there is provided a process for hydrogenating an ester group in a cyclic or acyclic saturated aliphatic mono- or dicarboxylic ester, thereby converting the acid moiety of said ester to a primary alcohol group, said acid moiety containing at least two carbon atoms, comprising contacting a solution of hydrogenation catalyst and said ester neat or in an inert solvent therefore, with an atmosphere containing hydrogen gas, at a temperature of about 0° to 150° C., under a pressure of about 0 to 150 psig, said catalyst being a composition of the formula:

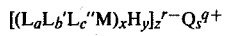

$$[(L_a L_b' L_c'' M)_x H_y]_z{}^{r-} Q_s{}^{q+}$$

including dimers, trimers and tetramers thereof, wherein L, L' and L'' are independently selected from organoligands containing phosphorus, arsenic or antimony elements, each ligand being free of carbonyl and containing at least one said element, M being a Group VIII metal, H being hydrido, Q being acation, wherein a, b and c are integer values of 0 or 1, the sum of a, b, c being of from 1 to 3, x being a value 1 or 2, y being an integer value of from 1 to 3x, x being defined above, r and s independently being integer values of 1 or 2, and z and q independently being integer values of from 1 to 3, wherein said composition is electrically neutral and contains a minimum of one and a maximum of three atoms of phosphorus, arsenic, antimony, or mixtures thereof, per Group VIII metal atom.

Further provided is a process for decarbonylating an alkyl formate ester thereby producing an alkyl alcohol and carbon monoxide comprising contacting said alkyl formate ester with the catalyst composition described hereinabove, neat or in an inert solvent therefor, at a temperature of about 0° to 150° C., under a dry atmosphere.

DESCRIPTION OF INVENTION AND PREFERRED EMBODIMENTS

The novelty of the invention process resides in the fact that the anionic Group VIII metal hydride compositions described in U.S. Application 972,147 by Guido Pez and Roger Grey, hereby incorporated by a reference, are very efficient catalysts for the hydrogenation of carboxylic esters thus producing the corresponding primary alcohols. A complete and thorough description of the anionic hydride compositions, their structure, synthesis and physical properties thereof, are adequately described in the above-mentioned reference. For purposes of this invention, the scope of the compositions useful as catalysts in the instant invention process is identical to the scope of the compositions disclosed in the above-described reference. By the terms "hydrogenation catalyst" and "catalyst composition" as used herein, is meant the compositions described above.

The Group VIII metals present in the compositions useful as catalysts in the invention process include iron, cobalt, nickel, ruthenium, rhodium, palladium, osmium, iridium and platinum and preferably ruthenium, rhodium, iron, and platinum, designated as M in the above-described formula.

Organoligands, independently designated L, L' and L'', present in the compositions include the coordinating elements phosphorus, arsenic and antimony and preferably those of phosphorus and arsenic. The number of ligands present is 1 to 3 per Group VIII metal atom, designated by the sum of a, b, and c, and the value of x, in which each ligand is carbonyl free and contains at least one P, As or Sb element, and included in the total number of ligands, is a maximum of three atoms of said elements present per Group VIII metal atom in the molecule. A maximum of three atoms of P, As or Sb, or mixtures thereof, per Group VIII metal atom is a limitation because we believe that more than this number interferes in the catalytic process. For example, it has been found by us that when the anionic tris (triphenylphosphine)ruthenium complex, is employed during the homogeneous catalytic hydrogenation of ketones or esters, additional triphenylphosphine has an adverse effect upon catalytic reactivity, wherein we believe the anionic tetrakis(triphenylphosphine)ruthenium complex is formed under the conditions.

It is also considered that carbonyl ligands generally withdraw electronic charge from the respective metal atom, to which they are attached, thus rendering any hydride ligand attached to the metal atom less hydridic in character. Since it is considered that the effectiveness of the subject compositions as homogeneous catalysts is a function of the hydridic nature of the hydride ligands, the subject compositions do not contain carbonyl ligands. Further, we have found that the presence of carbon monoxide acts as a catalyst poison in the homogeneous hydrogenation of esters utilizing the catalyst compositions described herein.

Included among ligands applicable in the compositions are those wherein L, L' and L" are independently of the formulae:
(R'R"G$_1$), (R'R"R'''G$_1$) or (R'R"G$_1$—R—G$_2$R'''R'''') wherein G$_1$ and G$_2$ are independently phosphorus, arsenic or antimony and R', R", R''' and R'''' are independently selected from C$_1$-C$_{18}$ linear or branched alkyl, phenyl, C$_1$-C$_{18}$ linear or branched alkylphenyl and phenyl-substituted C$_1$-C$_{18}$ linear or branched alkyl, and R being a C$_1$-C$_4$ divalent alkyl bridging group between G$_1$ and G$_2$, wherein said alkyl and phenyl groups can also be substituted with groups inert toward metal arenes (such as potassium naphthalene), such as C$_1$-C$_4$ alkoxy, being linear or branched, and the like. Bidentate ligands are considered as being one ligand in the above-described formula for the subject compositions and may form two points of attachment per Group VIII metal atom, or be bridged between two Group VIII metal atoms.

Representative examples of organoligands applicable in the compositions (Ph being used hereinafter to designate phenyl) are triphenylphosphine (Ph$_3$P), diphenylmethylphosphine (Ph$_2$CH$_3$P), diphenylphosphide (Ph$_2$P), triphenylarsine (Ph$_3$As), diphenylmethylarsine (Ph$_2$CH$_3$As), trimethylphosphine, triethylphosphine, trioctadecylphosphine, tri-n-octylphosphine, triisopropylphosphine, tri-secondary-butylphosphine, tricyclohexylphosphine, tri(pentamethylphenyl)phosphine, tri(p-tolyl)phosphine, tri(p-n-octadecylphenyl)phosphine, tri(p-n-octylphenyl)phosphine, tri(2-phenethyl)phosphine, tribenzylphosphine, tri(2-phenyl-isooctadecyl)phosphine, tri(p-methoxyphenyl)phosphine, tri(2-methoxyethyl)phosphine, tri(p-tertiary-butoxyphenyl)phosphine, triphenylstibine, dimethylphosphinoethane (Me$_2$PCH$_2$CH$_2$PMe$_2$) and diphenylphosphinoethane (Ph$_2$PCH$_2$CH$_2$PPh$_2$).

Preferred ligands are those of organophosphorus and organoarsine types and particularly preferred are those of organophosphorus, particularly triphenylphosphine, diphenylmethylphosphine and diphenylphosphide.

The charge on the anion in the composition, designated as r, can be −1 or −2, and the number of anions in the composition, designated by z, can be from 1 to 3.

Cation Q in the composition has a positive charge from +1 to +3 designated by q, and the composition can have from one to three cations, designated by s. Representative examples of cations applicable in the composition include the Group IA alkali metals, such as Li, Na, K, Rb and Cs, the Group IIA alkaline earth metals, such as Be, Mg, Ca, Ba and Sr, Group IIIA metals such as Al, and Ga, divalent and trivalent lanthanide elements such as La$^{+3}$ and Eu$^{+2}$, "metallocene" sandwich-type organo-metallic gegencations, such as (C$_5$H$_5$)$_2$Ti$^+$, and (C$_5$H$_5$)$_2$V$^+$, and divalent transition metals such as V, Cu, Mn and Fe. Preferred cations in the compositions are K$^+$, Li$^+$, La$^{+3}$ and V$^{+2}$. The total cationic and anionic charges in the composition are equivalent in absolute value such that the resulting composition is electrically neutral.

The number of hydrogen atoms also termed "hydride" or "hydrido" ligands, attached to the Group VIII metal atoms in the compositions is from 1 to 3x, ("x" being defined above) designated by the symbol y, and can be from 1–6 and preferably two or four. It is believed that where one hydrogen atom is present per two Group VIII metal atoms, the hydrogen atom is bridged between the two respective metal atoms. One of the hydride ligands present can be formed by an ortho metallation process as described below. The number of hydride ligands is easily established in the molecule by the well-known technique of reacting one gram mole of said composition in a pure state with at least about one gram-mole of hydrogen chloride, producing one gram-mole of hydrogen gas per gram-atom of hydride ligand present in the composition. Stoichiometrically, the reaction requires one gram-mole of hydrogen chloride, but in practice, a slight excess over this amount is used to insure complete reaction.

Representative examples of compositions applicable in the process are illustrated by the following formulas which are approximate structural formulas, as regarded by us, on the basis of present available evidence:

[(Ph$_3$P)$_3$RuH]$^-$K$^+$; [(Ph$_3$P) (Ph$_2$P)RuH]$_2$$^-$K$_2$$^+$;
](Ph$_3$P)$_2$RuH]$^-$K$^+$;
[(Ph$_2$P)$_2$Fe$_2$H]$^=$K$_2$$^+$, [(Ph$_3$P)$_3$RuH]$^-$Na$^+$;
[(Ph$_3$P)$_3$RuH]$^-$Li$^+$;
[(Ph$_3$P)$_3$RuH]$_2$$^-$Mg$^{+2}$; [(Ph$_3$P)$_2$RuH]$^-$Li$^+$;
[(Ph$_3$P)$_2$RuH]$^-$Cs$^+$;
[(Ph$_2$CH$_3$P)$_3$RuH]$^-$K$^+$; [(Ph$_3$P)$_2$PtH]$^-$K$^+$;
[(Ph$_3$P)$_3$RhH]$^-$K$^+$;
[(Ph$_3$P)$_2$RuH$_2$]$^-$K$^+$; [(Ph$_3$P)$_2$RuH$_3$]$^-$K$^+$.

Preferred compositions for use in the process are listed below giving their approximate structural formulas, assigned Roman numerals, used herein for convenient referral thereto, and chemical names.

| Formula | Roman Numerals | Chemical Name |
|---|---|---|
| [(Ph$_3$P)$_3$RuH]$^-$K$^+$ | I | potassium tris(triphenyl phosphine) ruthenium hydride |
| [(Ph$_3$P) (Ph$_2$P) RuH]$^-$K$^+$ | II | potassium triphenylphosphine diphenylphosphide ruthenium hydride |
| [(Ph$_3$P)$^2$RuH]$^-$K$^+$ | III | potassium bis(triphenylphosphine)ruthenium hydride |

The molecular structure of the compositions are fairly complex and have only been rigorously studied in detail in a few cases. For example, structure (I) behaves chemically as a dihydride and, on the basis of its infrared and nuclear magnetic resonance spectra and chemical properties, can be more properly represented as being ortho-metallated by the formula:

In the case of compound (II) it is felt that ortho-metallation occurs, but it is not shown in the formula since it is not known which specific phosphine (or phosphide) moiety is in fact ortho-metallated. We have shown that on the basis of chemical reactivity that the compound is a dihydride and also on the basis of proton and $-P$ nuclear magnetic resonance spectra that the compound is a dimer. Thus, for purposes of this disclosure, the following approximate structural formulas are considered to be equivalent:

$[(Ph_3P)_2(Ph_2P)_2 Ru_2H_4]^= K_2^+$;
$[(Ph_3P) (Ph_2P)RuH_2]_2^- K_2^+$;
$[(Ph_3P) (Ph_2P)RuH]_2^- K_2^+$; and
$[(Ph_3P) (Ph_2P)RuH]^- K^+$.

It is believed that the subject compositions can also exist in dimer, trimer and tetramer forms of their basic empirical formulas.

It is not clearly understood, but is felt that the compositions possess the ability to undergo "ortho-metallation", a process whereby an "unfilled" coordination site on the Group VIII metal atom becomes attached by substitution onto the ortho position of a neighboring phenyl radical, as present in triphenylphosphine. The bond formation between the metal atom and the ortho carbon on the phenyl ring displaces the ortho hydrogen atom which then attaches to the metal atom thus forming a dihydride as indicated by the horizontal bracket on the above-described formula. It is considered that "ortho-metallation" in solution, is a dynamic, reversible process in which the ortho-metallated material can react back to the non-ortho-metallated form. This ortho-metallation behavior may be present in the other catalyst compositions and can be observed by a dihydride behavior of the substance in that one gram-atom of hydride ligand in the catalyst composition will liberate one gram-mole of hydrogen gas upon reaction with at least about one gram-mole of hydrogen chloride.

Other chemical characteristics of the catalyst compositions are that one gram-atom of hydrido ligand in the subject composition will liberate one gram-mole of methane upon reaction with at least about one gram-mole of methyl iodide.

The infrared spectra of the compositions exhibit metal-hydride absorption maxima in the infrared region of about 1600 to 1900 cm$^{-1}$ and usually about 1750 to 1850 cm$^{-1}$.

The catalyst compositions can exist in the "free form" as described by the above structural formula and can also exist wherein the cation is complexed with an organic solvent in adduct form, or as a complex with a chelating agent for said cation. For example, structure I can exist as an etherate, being complexed with one mole of diethyl ether per mole of composition. The catalyst composition can also form adducts with aromatic hydrocarbons, such as naphthalene and toluene and chelates with chelating agents, such as crown ethers, e.g. 18-crown-6, cryptates, being bicyclic-nitrogen bridged diamines having oxyethylene bridges, such as 2,2,2-crypt, and the like. Adducts and chelates of the compositions, in some cases, display better crystalline properties than the free-form composition, and are more convenient for handling and operability. However, for purposes of this invention the free-form composition and adducts and chelates thereof, are considered to be equivalents as compositions and within the scope of the applicable compositions.

The anionic Group VIII metal hydride compositions applicable herein can be prepared by reacting a neutral Group VIII metal complex, metal halide, hydridohalide or hydride, with a metal cationic radical anion complex, hereinafter referred to as "metal arene," such as potassium naphthalene, in a suitable solvent, such as tetrahydrofuran or diethylether, at a temperature of about $-111°$ C. to $+80°$ C., under vacuum or under an inert atmosphere. The product is easily isolated and purified from the reaction mixture. A description of apparatus found useful in preparing the composition is described in J. Amer. Chem. Soc., 98, 8072 (1976), hereby incorporated by reference.

Carboxylic acid esters, comprised of an acid moiety and alcohol moiety, and by the term "alcohol moiety", is meant to include aromatic hydroxy moiety, e.g., phenols and naphthols as well, which are applicable in this invention process, include those wherein the acid moiety is derived from a $C_2$–$C_{18}$ linear or branched alkyl monocarboxylic acid, $C_2$–$C_6$ linear or branched alkyl dicarboxylic acid, $C_7$–$C_8$ cycloalkyl monocarboxylic acid, $C_2$–$C_4$ fluorinated monocarboxylic acid, containing 1–7 fluorine atoms, and said alcohol moiety of said ester is derived from a $C_1$–$C_4$ linear or branched alkyl alcohol, $C_1$–$C_4$ linear or branched fluorinated alcohol, containing 1–7 fluorine atoms, $C_7$–$C_9$ aralkyl alcohol, or $C_6$–$C_{10}$ aromatic hydroxy compound.

Representative examples of carboxylic acids providing the acid moiety in said ester are acetic acid, propionic acid, butyric acid, isobutyric acid, n-hexanoic acid, n-heptanoic acid, n-octanoic acid, n-nonanoic acid, n-decanoic acid, n-pentadecanoic acid, n-octadecanoic acid, oxalic acid, malonic acid, succinic acid, adipic acid, cyclohexylcarboxylic acid, cyclohexylacetic acid, fluoroacetic acid, difluoroacetic acid, trifluoroacetic acid, trifluoropropionic acid and trifluorobutyric acid, and the like.

Representative examples of alcohols and aromatic hydroxy compounds providing the alcohol moiety in said ester are methanol, ethanol, propanol, isopropanol, n-butanol, isobutanol, sec-butanol, t-butanol, 2,2,2-trifluoroethanol (hereinafter referred to as "trifluoroethanol"), monofluoromethanol, difluoromethanol, 1,3-difluoro-2-propanol, benzyl alcohol, phenethyl alcohol, phenol, 2-naphthol, and the like.

It is to be understood that esters produced from combinations of the above-described acids and alcohols in known manner are deemed to be applicable within the scope of this invention process. Representative examples of esters useful in the invention process are methyl acetate, ethyl acetate, methyl n-octadecanoate, isobutyl decanoate, t-butylnonoate, phenyl acetate, 2-naphthyl propionate, dimethyl oxalate, diethyl oxalate, dimethyl malonate, diethyl malonate, dimethyl succinate, diethyl succinate, dimethyl adipate, diethyl adipate, methyl cyclohexylcarboxylate, ethyl cyclohexylacetate, n-butyl fluoroacetate, methyl difluoroacetate, n-propyl trifluoropropionate, methyl trifluorobutyrate, isopropyl acetate, sec-butyl propionate, fluoromethyl acetate, difluoromethyl acetate, 1,3-difluoro-2-propyl octanoate, benzyl acetate, phenethyl acetate, methyl trifluoroacetate and trifluoroethyl trifluoroacetate. Preferred examples of esters in the invention process are dimethyl oxalate, methyl acetate, ethyl acetate, methyl propionate, methyl trifluoroacetate and trifluoroethyl trifluoroacetate. Particularly preferred ester in the invention process is trifluoroethyl trifluoroacetate.

The hydrogenation of the carboxylic acid ester group in a compound in the process leads to the production thereby of primary alcohol, produced from the carboxylic acid moiety, and regeneration of the alcohol or aromatic hydroxy compound from the alcohol moiety in the ester. In the case of dicarboxylic acid esters, the invention process leads to hydrogenation of generally only one ester group, at temperatures below 150° C. and pressures below 150 psig, thus producing mainly the mono-alcohol-mono-ester, as in the case of dimethyl oxalate in which methyl glycolate is the principal product. It is considered that more forcing conditions, i.e. temperatures higher than 150° C. and pressures higher than 150 psig, will result in hydrogenation of both ester groups thus yielding a diol.

In addition to the esters described hereinabove, cyclic "inner esters", i.e. lactones, are also applicable in the invention process, which can be hydrogenated to yield diols, useful in the synthesis of polyesters. The scope of lactones applicable in the invention process include $C_3-C_{12}$ alkyl lactones, such as propiolactone, butyrolactone, valerolactone, octanoic lactone, caprolactone and 1,12-dodecalactone. Preferred are alkyl lactones in which the lactone functional group is formed between the first and terminal carbon atoms in the precursor hydroxy alkyl carboxylic acid. Thus, butyrolactone canbe hydrogenated to yield, 1,4-butanediol and the above-described lactones will yield diols in like manner.

The amount of carboxylic acid ester substrate present in the process is not critical and is generally about 1 to 100,000 parts by weight of substrate per part of catalyst composition and preferably, about 10 to 1,000 parts by weight of ester substrate per part of catalyst composition. However, larger or smaller amounts of substrate may effectively be used.

The process can be conducted in the neat state, i.e. no solvent, providing said ester is liquid at the reaction temperature employed and the catalyst is soluble therein. However, it is preferred to conduct the reaction in the presence of an inert solvent for both the carboxylic ester substrate and catalyst composition. The solubility of the respective materials in the solvent should be significantly large enough to initiate and maintain the hydrogenation process.

Solvents which are applicable in the invention process must be inert toward hydrogenation under the reaction conditions and possess adequate solvating ability for the substrate carboxylic acid ester and catalyst, should preferably be anhydrous, and include $C_6-C_{12}$ non-fused benzenoid hydrocarbons, and $C_2-C_{18}$ alkyl derivatives thereof, $C_5-C_{10}$ linear or branched saturated aliphatic or alicyclic hydrocarbons, $C_4-C_6$ saturated aliphatic cyclic mono- or diethers and $C_2-C_6$ linear or branched saturated aliphatic mono- or diethers, $C_7-C_{14}$ aromatic ethers, or mixtures thereof. By the term "non-fused benzenoid hydrocarbon" is meant that if more than one benzene ring is present in the hydrocarbon, they are not fused together. Thus, the term includes biphenyl but not naphthalene.

Representative examples of specific solvents useful in the invention process are benzene, toluene, xylene, hexamethylbenzene, biphenyl, n-octadecylbenzene, pentane, cyclopentane, cyclohexane, methylcyclohexane, hexane, isooctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenyl ether, and mixtures thereof.

Preferred solvents in the invention process are toluene, benzene, cyclohexane, hexane, tetrahydrofuran, p-dioxane, diethyl ether or 1,2-dimethoxyethane. Particularly preferred solvents are benzene and toluene. Preferred solvents for the hydrogenation of $C_2-C_{18}$ linear or branched alkyl monocarboxylic acids are the relatively non-polar hydrocarbons, described above, particularly toluene.

The amount of solvent, when used, is not critical provided sufficient solvent is present to dissolve the carboxylic acid ester substrate and catalyst and to initiate and maintain the hydrogenation reaction. In general, about 1 to 100 parts by weight of solvent per part of ester is used, although not limited thereto, larger or smaller amounts being effective with the above proviso.

As described above, the composition catalysts exist in the free form or can be present as an adduct or chelate with another organic molecule. Chelating agents of the type described above may be employed, such as crown ethers, including 15-crown-5, 18-crown-6, dibenzo and dicyclohexyl derivatives thereof; cryptates, such as 2.2.2-crypt, hexacyclen, the nitrogen analog of 18-crown-6 crown ether, and tertiary amines such as N,N,N'-tetramethylethylenediamine and the like. A preferred chelating agent is 18-crown-6. If a chelating agent is used, normally it is used in a molar ratio of chelating agent to catalyst of about 1:1 to 2:1 and preferably in slight excess over the stated 1:1 molar ratio.

In general, the hydrogenation of esters with the catalyst compositions may be sensitive to the solvent or additive used to complex the cation. It is preferred to use the non-fused benzenoid hydrocarbons in the hydrogenation of the above-described $C_2-C_{18}$ alkyl esters, and preferably in the absence of chelating agents. It is also preferred to utilize chelating agents in the hydrogenation of dicarboxylic esters, and particularly dimethyl oxalate. Fluorine-containing carboxylic esters are hydrogenated equally well in non-polar and polar solvents, described above, and in the presence of chelating agents. However, it is preferred to utilize the non-polar solvents described above, for the hydrogenation in the absence of chelating agents, since the rate of hydrogenation is usually faster, such as for trifluoroethyl trifluoroacetate.

Temperature in the process is normally in the range from about 0° C., to about 150° C. and preferably in the range of about 80° to 100° C. However, higher temperatures under more severe conditions can also be employed and are considered to be equivalent to the stated preferred ranges.

The pressure in the reaction process is usually about 0 psig (101 to 1135 KPa absolute) to 150 psigat the reaction temperature and preferably at about 80 to 100 psig (653 to 690 KPa absolute) at the reaction temperature. However, higher pressures under more severe conditions can be employed and are considered to be equivalent to the stated preferred ranges. The term "psig" refers to pounds per square inch gauge and 0 psig corresponds to 1 atmosphere, and 150 psig corresponds to about 11 atmospheres.

The process is conducted under an atmosphere containing hydrogen gas, being the active reducing agent. The atmosphere above the reaction mixture can also contain an inert gas such as nitrogen, argon, mixtures thereof, and the like, as long as sufficient hydrogen gas is present to maintain the hydrogenation reaction. It is preferred to conduct the process under an atmosphere consisting essentially of hydrogen gas, and particularly preferred at a pressure of about 80–100 psig.

Conversions of esters in the process range from 30 to 100% of theory based on the starting amount of ester substrate.

Selectivities in the process for production of primary alcohols from esters is in the range of about 90 to 100%, being defined as (moles primary alcohol produced/divided by moles ester hydrogenated) × 100.

The invention process can be modified for a batch type process for fluorinated esters wherein the catalyst is recycled after use in one run. After the process has been conducted, the product, solvent and volatiles are removed by distillation under reduced pressure and fresh solvent added and the resulting solution stirred under about 5 to 10 psig of hydrogen gas for about 5 to 10 minutes. The solution is then preferably frozen and hydrogen removed by distillation under reduced pressure. Fresh substrate is then added and the reaction process run through another cycle. By performing this recycled step, catalyst from the original run can be used for about 4 to 5 additional runs.

In the case of easily hydrogenated esters, such as the fluorine-containing alkyl esters, further recycle can be conducted by employing a catalyst regeneration agent. Said regeneration agent has the formula $CBH(OR)_3$ or $CBHR_3$, where R is $C_1$–$C_4$ linear or branched alkyl including methyl, ethyl, propyl, isopropyl, n-butyl, isobutyl, sec-butyl and n-butyl, and C is lithium, sodium, potassium or cesium cation. Preferred agent is sodium trimethoxy borohydride. The regeneration procedure is generally conducted after a run by distilling off all solvent and volatile materials. The regeneration agent is then added in an amount of about 3:1 to 7:1 molar ratio of agent to said catalyst. An ether, such as tetrahydrofuran or glyme, is added and the resulting solution stirred under reduced pressure at room temperature for about 1 hour. The ether and other volatiles are removed by distillation under reduced pressure leaving dry catalyst and agent residue. Solvent and new ester substrate are then added and a new run is commenced. Addition of regeneration agent prolongs catalyst life times such that about 20–50 additional runs of the reaction process can be conducted.

The product primary alcohol can be isolated from the process and purified by conventional methods such as extraction, followed by fractional distillation or column or gas chromatographic techniques.

Also a subject of this invention is a process for decarbonylating an alkyl formate ester to an alkyl alcohol and carbon monoxide as illustrated in the following reaction scheme:

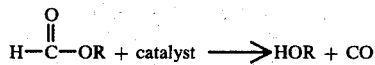

The process comprises contacting an alkyl formate ester with the catalyst described herein, being neat or in an inert solvent therefor, under a dry atmosphere, at a temperature of about 0° to 150° C., thereby resulting in the corresponding alkyl alcohol and carbon monoxide respectively.

The process variables in this process are identical to the first-described process for hydrogenation of an ester with respect to temperature, pressure, solvent, catalyst composition, catalyst and solvent concentration, catalyst recycle and apparatus and need not be reiterated. The main difference between the two processes are that an atmosphere containing hydrogen gas is not required, for formate decarbonylation inert gases such as nitrogen, argon or solvent vapor being sufficient.

Formates which are applicable in this process are alkyl formates, wherein the alkyl radical therein being $C_1$–$C_{18}$ linear or branchedalkyl wherein said alkyl radical can also be substituted with groups inert under the reaction conditions such as $C_1$–$C_4$ linear or branched alkyl or $C_1$–$C_4$ linear or branched alkoxy.

Representative examples of formates applicable in the process are methyl formate, ethyl formate, isobutyl formate, isoamyl formate, octyl formate and the like.

Preferred method for carrying out the decarbonylation process is where $[(Ph_3P)_3RuH]^-K^+$ is the catalyst, the reaction is conducted neat, 80°–100° C. is the temperature, 50–70 psig is the pressure, in an argon atmosphere, and said reaction is carried out for about 16 hours thereby resulting in the corresponding alcohol and generated carbon monoxide. Pressure in the process will of course increase due to the generation of carbon monoxide and the pressure in the reaction will increase above initial pressure to about 200 to 300 psig.

Apparatus for conducting the invention process can be any conventional pressure apparatus, glass or steel, in which the operations of charging the reactant materials, heating, cooling, stirring, introduction of hydrogen gas, isolation and purification the final products can be conducted substantially in the absence of air and moisture. Such apparatus and procedure for carrying out the invention process will be obvious to one skilled in the art from this disclosure.

The following examples are illustrative of the best mode of carrying out the invention as contemplated be us and should not be construed as being limitations on the scope and spirit of the instant invention.

EXAMPLE 1

Catalytic Hydrogenation of Dimethyl Oxalate

A glass pressure tube was charged with 40 mg of the bis-phosphine catalyst $[(Ph_3P)(Ph_2P)RuH_2]_2^-K_2^+$, (prepared by reacting bis(triphenylphosphine)ruthenium hydridochloride.toluene dimer with potassium naphthalene in about a 1:2 molar ratio in tetrahydrofuran at about −80° C. underreduced pressure), 0.5 gram (4.23 mmol) of dimethyl oxalate and 5 ml of toluene. The reaction solution was pressurized with 100 psig of hydrogen and allowed to react in the absence of moisture and molecular oxygen at 90° C. for 16 hours. Gas chromatographic analysis of the reaction mixture showed 95% conversion of the dimethyl oxalate to methanol and methyl glycolate as the only products.

EXAMPLE 2

Catalytic Hydrogenation of Methyl Acetate

A glass pressure tube was charged with 40 mg of the bis-phosphine catalyst described in Example 1, 0.47 gram (6.3 mmol) of methyl acetate and 5 ml of toluene. The reaction solution was pressurized with 100 psig of hydrogen and allowed to react at 90° C. for 16 hours. Gas chromatographic analysis of the reaction mixture showed 35% conversion of the methyl acetate to methanol, ethanol and ethyl acetate as the only products.

EXAMPLE 3

Catalytic Hydrogenation of Methyl Trifluoroacetate

A glass pressure tube was charged with 20 mg of the bis-phosphine catalyst described in Example 1, 0.72 gram (5.6 mmol) of methyl trifluoroacetate and 3 ml of toluene. The reaction solution was pressurized with 90 psig of hydrogen and allowed to react in the absence of moisture and molecular oxygen at 90° C. for 16 hours. Gas chromatographic analysis of the reaction mixture showed 88% conversion of the methyl trifluoroacetate to 2,2,2-trifluoroethanol and methanol in a selectivity of about 98%.

EXAMPLE 4

Catalytic Hydrogenation of Trifluoroethyl Trifluoroacetate (a) Hydrogenation

A glass pressure tube was charged with 20 mg of the bis-phosphine catalyst described in Example 1, 1.1 gram (5.7 mmols) of trifluoroethyl trifluoroacetate and 3 ml of toluene. The reaction solution was pressurized with 90 psig of hydrogen and allowed to react in the absence of moisture and molecular oxygen at 90° C. for 4 hours. Gas chromatographic analysis of the reaction mixture showed 99% conversion of the ester to 2,2,2-trifluoroethanol in a selectivity of about 98%.

(b) Catalyst Recycle of Trifluoroethyl Trifluoroacetate

Trifluoroethanol and toluene were removed from the above reaction mixture by vacuum distillation at room temperature. Toluene (3 ml) was distilled into the pressure tube containing the dry catalyst residue and this solution stirred under 5 psig of hydrogen for 5 minutes. The solution was frozen, the hydrogen pumped off and 1.1 gram (5.7 mmols) of trifluoroethyl trifluoroacetate distilled in under vacuum. The resulting solution was warmed to room temperature under a hydrogen atmosphere, pressurized to 90 psig of hydrogen and allowed to react at 90° C. for 7 hours. The resulting product mixture was analyzed by gas chromatography and showed a 99% conversion and 98% selectivity for trifluoroethanol.

(c) Catalyst Regeneration

After five cycles similar to the one described above, the gas chromatographic analysis showed only 80% conversion to trifluoroethanol and the catalyst was then regenerated in the following manner. The pressure tube containing the catalyst residue (originally 0.03 mmol) was charged with 20 mg (0.25 mmol) of $NaBH(OCH_3)_3$, in a dry box. Tetrahydrofuran (3 ml) was distilled into the tube under vacuum and the solution stirred at room temperature for one hour. The solvent and other volatiles were removed in vacuo and the residue evacuated to dryness. The pressure tube was then charged with toluene (3 ml) and 1.1 gram (5.7 mmols) of ester and the hydrogenation was conducted as described in part (a).

In subsequent catalyst recycles, the concentration of ester was gradually increased to 50% volume/volume in toluene, then neat ester was finally used. A lifetime study included 22 catalyst recycles and four regeneration steps in which the equivalent of 3400 gms of ester were reduced per gram of original catalyst present.

EXAMPLE 5

The following runs were made utilizing the apparatus and procedure as described in Example 1. The pressure of hydrogen gas used in the runs was 90 psig and the temperature in each run was conducted at 90° C. for a period of not more than 16 hours. The following table lists and summarizes the alkyl ester substrate used, the solvent, chelating agent if used, and calculated N number in the process for the product resulting from the hydrogenation.

TABLE I
Catalytic Hydrogenation of Esters*

| Catalyst+ | Substrate | Solvent | Additive | N | Remarks |
|---|---|---|---|---|---|
| II | Methyl acetate[a] | THF | | 2 | |
| " | " | toluene | | 38 | |
| " | " | toluene | 18-crown-6 | 2 | e |
| I | Dimethyl oxalate[b] | THF | | 6 | |
| " | " | toluene | | 20 | |
| II | " | THF | | 2 | |
| " | " | THF | KBr | 80 | f |
| " | " | toluene | | 80 | |
| " | " | toluene | 18-crown-6 | 80 | f |
| " | Methyl Trifluoroacetate[c] | THF | | 100 | |
| " | Methyl Trifluoroacetate[c] | toluene | | 100 | g |
| " | Methyl Trifluoroacetate[c] | toluene | 18-crown-6 | 75 | h |
| I | Trifluoroethyl Trifluoroacetate[d] | toluene | | 40 | |
| IV | Trifluoroethyl Trifluoroacetate[d] | toluene | | 40 | |
| V | | toluene | | 40 | |
| II | Trifluoroethyl Trifluoroacetate[d] | toluene | | 180 | |
| " | Trifluoroethyl Trifluoroacetate[d] | toluene | 18-crown-6 | 120 | h |
| " | Trifluoroethyl Trifluoroacetate[d] | neat ester | | 460 | |
| " | Trifluoroethyl Trifluoroacetate[d] | neat ester | | 390 | |

*catalyst conc. = 0.01M; volume of system = 98 cc; concentration of substrate: a = 1.26M, b = 1.1M, c and d = 1.84M. Remarks: e = additive inhibits reaction, f = additive promotes reaction, g = initial rates are faster than THF reaction, h = additive decreases rate; N = number of moles of ester hydrogenated per mole of catalyst in one batch reaction.

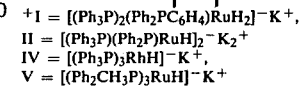

+I = $[(Ph_3P)_2(Ph_2PC_6H_4)RuH_2]^-K^+$,
II = $[(Ph_3P)(Ph_2P)RuH]_2^-K_2^+$
IV = $[(Ph_3P)_3RhH]^-K^+$,
V = $[(Ph_2CH_3P)_3RuH]^-K^+$

EXAMPLE 6

Catalytic Decarbonylation of Ethyl Formate

A glass pressure tube was charged with 40 mg of bright yellow tris-phosphine catalyst,

$[(Ph_3P)_2(Ph_2PC_6H_4)RuH_2]^-K^+$, produced by reacting tris(triphenylphosphine)ruthenium hydridochloride with potassium naphthalene in about 1:2 molar ratio in tetrahydrofuran at −80° C. under reduced pressure, and 4 grams (54 mmols) of ethyl formate. The reaction was pressurized with 50 psig of hydrogen. The reaction solution was stirred at 90° C. for two hours and the pressure increased to 235 psig. Gas chromatographic analysis of the reaction mixture showed ethanol and carbon monoxide as the only products produced in a 92% conversion. Methyl formate under similar conditions was decarbonylated in a conversion of about 90%.

The hydrogenation of dimethyl adipate was unsuccessfully attempted in toluene solvent at 90° C. in the presence of the bis-phosphine catalyst described in Example 1. However, we believe that dimethyl adipate ester can be reduced under other conditions as described herein, and thus regard adipate ester as being also within the scope of the invention process.

We claim:

1. A process for hydrogenating an ester selected from the group consisting of methyl acetate, ethyl acetate, methyl propionate, methyl trifluoroacetate, trifluoroethyl triflouroacetate and dimethyl oxalate, comprising contacting a solution of hydrogenation catalyst and said ester, neat or in an inert solvent therefor, with an atmosphere containing hydrogen gas, at a temperature of about 0° to 150° C., under a pressure of about 0 to 150 psig (101 to 1135 kPa absolute) of gaseous hydrogen, said catalyst being of the group consisting of potassium tris (triphenylphosphine) ruthenium hydride, potassium triphenylphosphine diphenylphosphide ruthenium hydride, potassium tris (triphenylphosphite) ruthenium hydride, potassium tris triphenylphosphine rhodium hydride, and potassium tris (methyldiphenylphosphine) ruthenium hydride.

2. Process of claim 1 wherein any inert solvent employed is toluene.

3. Process of claim 2 wherein the ester hydrogenated is methyl acetate.

4. Process of claim 2 wherein the ester hydrogenated is dimethyl oxalate.

5. Process of claim 2 wherein the ester hydrogenated is methyl trifluoroacetate.

6. Process of claim 2 wherein the ester hydrogenated is trifluoroethyl trifluoroacetate.

7. Process of claim 6 wherein the catalyst is potassium triphenylphosphine diphenylphosphide ruthenium hydride.

8. Process of claim 7 further comprising regenerating the catalyst by action of sodium trimethoxy borohydride.

* * * * *